United States Patent
Zong et al.

(10) Patent No.: US 9,788,793 B2
(45) Date of Patent: Oct. 17, 2017

(54) METHOD AND SYSTEM TO IDENTIFY MOTION ARTIFACTS AND IMPROVE RELIABILITY OF MEASUREMENTS AND ALARMS IN PHOTOPLETHYSMOGRAPHIC MEASUREMENTS

(71) Applicant: KONINKLIJKE PHILIPS N.V., Eindhoven (NL)

(72) Inventors: Wei Zong, Belmont, MA (US); Dale Wiggins, Methuen, MA (US); Brian David Gross, North Andover, MA (US); Larry Nielsen, Burlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 73 days.

(21) Appl. No.: 14/417,275

(22) PCT Filed: Jul. 22, 2013

(86) PCT No.: PCT/IB2013/055999
§ 371 (c)(1),
(2) Date: Jan. 26, 2015

(87) PCT Pub. No.: WO2014/020484
PCT Pub. Date: Feb. 6, 2014

(65) Prior Publication Data
US 2015/0190096 A1 Jul. 9, 2015

Related U.S. Application Data

(60) Provisional application No. 61/678,132, filed on Aug. 1, 2012.

(51) Int. Cl.
*A61B 5/00* (2006.01)
*A61B 5/024* (2006.01)
(Continued)

(52) U.S. Cl.
CPC .......... *A61B 5/721* (2013.01); *A61B 5/0205* (2013.01); *A61B 5/02416* (2013.01); *A61B 5/11* (2013.01);
(Continued)

(58) Field of Classification Search
CPC ............................. A61B 5/721; A61B 5/7425
See application file for complete search history.

(56) References Cited

U.S. PATENT DOCUMENTS 5,025,791 A 6/1991 Niwa
5,368,026 A 11/1994 Swedlow et al.
(Continued)

FOREIGN PATENT DOCUMENTS

EP 2116183 A1 11/2009
JP 2007117601 5/2001
(Continued)

OTHER PUBLICATIONS

Asada, H. H., et al.; Active Noise Cancellation Using MEMS Accelerometers for Motion-Tolerant Wearable Bio-Sensors; 2004; IEEE EMBS; pp. 2157-2160.
(Continued)

*Primary Examiner* — Tammie K Heller (57) ABSTRACT

A system (10) and method to identify motion artifacts. Measurements of a physiological parameter of an associated patient are received from a probe (12) positioned on or proximate to the associated patient. Further, measurements of acceleration are received from an accelerometer (26) positioned on, proximate to, or integrated with the probe (12). Measurements of the physiological parameter are labeled based on the measured acceleration, such as being with or without motion.

17 Claims, 4 Drawing Sheets

(51) Int. Cl.
*A61B 5/11* (2006.01)
*A61B 5/0205* (2006.01)
*A61B 5/145* (2006.01)
*G01P 15/00* (2006.01)
*A61B 5/1455* (2006.01)
*A61B 5/021* (2006.01)

(52) U.S. Cl.
CPC ........ *A61B 5/1122* (2013.01); *A61B 5/14532* (2013.01); *A61B 5/14535* (2013.01); *A61B 5/14542* (2013.01); *A61B 5/14546* (2013.01); *A61B 5/746* (2013.01); *A61B 5/7425* (2013.01); *G01P 15/00* (2013.01); *A61B 5/02125* (2013.01); *A61B 5/02405* (2013.01); *A61B 5/14551* (2013.01); *A61B 2562/0219* (2013.01)

(56) References Cited

U.S. PATENT DOCUMENTS

| | | | |
|---|---|---|---|
| 5,827,196 A * | 10/1998 | Yeo | A61B 5/04525 128/901 |
| 6,879,850 B2 | 4/2005 | Kimball | |
| 7,957,781 B2 | 6/2011 | Mannheimer et al. | |
| 8,092,393 B1 | 1/2012 | Rulkov et al. | |
| 2004/0034293 A1 | 2/2004 | Kimball | |
| 2010/0125188 A1 | 5/2010 | Schilling et al. | |
| 2010/0298656 A1 | 11/2010 | McCombie et al. | |
| 2011/0316704 A1 * | 12/2011 | Nielsen | A61B 5/0002 340/573.1 |
| 2013/0116580 A1 * | 5/2013 | Liu | A61B 5/02 600/486 |

FOREIGN PATENT DOCUMENTS

| | | |
|---|---|---|
| JP | 2001-218746 | 8/2001 |
| JP | 2011098002 | 5/2011 |
| WO | 9422360 A1 | 10/1994 |

OTHER PUBLICATIONS

Han, H., et al.; Development of a wearable health monitoring device with motion artifact reduced algorithm; 2007; ICCAS; pp. 1581-1584.

Kim, S. H., et al.; Adaptive Noise Cancellation Using Accelerometers for the PPG Signal from Forehead; 2007; IEEE EMBS; pp. 2564-2567.

Wood, L. B., et al.; Noise Cancellation Model Validation for Reduced Motion Artifact Wearable PPG Sensors Using MEMS Accelerometers; 2006; IEEE EMBS; pp. 3525-3528.

* cited by examiner

METHOD AND SYSTEM TO IDENTIFY MOTION ARTIFACTS AND IMPROVE RELIABILITY OF MEASUREMENTS AND ALARMS IN PHOTOPLETHYSMOGRAPHIC MEASUREMENTS

CROSS REFERENCE TO RELATED APPLICATIONS

This application is a national filing of PCT application Serial No. PCT/IB2013/055999, filed Jul. 22, 2013, published as WO 2014/020484 A2 on Feb. 6, 2014, which claims the benefit of U.S. provisional application Ser. No. 61/678,132 filed Aug. 1, 2012, which is incorporated herein by reference.

BACKGROUND

The present application relates generally to physiological monitoring. It finds particular application in conjunction with pulse oximetry and will be described with particular reference thereto. However, it is to be understood that it also finds application in other photoplethysmographic measurement scenarios and is not necessarily limited to the aforementioned application.

Pulse oximetry is a non-invasive method allowing the monitoring of the oxygenation of a patient's hemoglobin. A sensor is placed on a thin part of the patient's body. In the case of an infant, the sensor is usually placed across a foot. Otherwise, the sensor is usually placed across a fingertip or an earlobe, or alternatively on the forehead. Light at red (e.g., around 660 nm) and infrared (e.g., around 940 nm) wavelengths is then passed sequentially through the patient to a photo-detector. The changing absorbance at each of the two wavelengths is measured to create a photoplethysmogram (PPG) for each of red light and infrared light.

Based on the PPGs, the absorbance due to the pulsing arterial blood alone, excluding venous blood, skin, bone, muscle, fat, fingernail polish (in most cases), and so on, can be determined. Using the ratio of changing absorbance of the red and infrared light caused by the difference in color between oxygen-bound (bright red) and oxygen-unbound (dark red or blue in severe cases) blood hemoglobin, a determination of oxygen saturation (SpO2) can be made. Oxygen saturation is the percentage of hemoglobin molecules bound with oxygen molecules to total hemoglobin (oxygenated and non-oxygenated).

Since pulse oximetry is non-invasive and convenient to use, it has become commonplace within hospital settings for patient monitoring, as well as in home healthcare settings. However, there are a number of conditions, due to the nature of photoplethysmographic measurement, which reduce the accuracy of the SpO2 calculation. This is also true for the calculations of percent saturated carboxyhemoglobin (SpCO), pulse rate (PR), pulse pressure variation (PPV), pulse transient time (PPT), hemoglobin (HB), hemocrit (HCT), glucose (GLU), cholesterol (CHOL), and any other physiological parameters derived by using photoplethysmographic measurements from the PPGs. This reduced accuracy, in turn, increases the number of false alarms.

One condition which reduces accuracy is low-perfusion (i.e., hypo-perfusion). Low-perfusion can, for example, cause falsely low SpO2 readings. However, this condition can be identified by analyzing the PPG signal itself so long as the PPG signal is clean (i.e., free of noise and/or artifacts). The user can then be notified of the condition, so the user knows that current measurements are inaccurate.

Another condition which reduces accuracy is movement of the sensor. When there is a movement with the sensor, the measuring condition is disturbed (i.e., the relationship between the absorbance from red and infrared photo sensors is no longer in the theoretically logical situation), so that the measurements from the movement period are no longer reliable and thus should not be used for, for example, display and/or alarming purpose to indicate one or more of SpO2, SpCO, PR, PPV, PPT, HB, HCT, GLU, and CHOL of the patient.

To compensate for motion artifacts requires identification of movement of the sensor and identification of those portions of the PPG signal associated with motion artifacts. One way to identify motion artifacts is to analyze the PPG signal and find atypical patterns. However, this is a challenging task because PPG patterns associated with pathophysiological situations and with motion artifacts can both vary over a wide range and overlap. Namely, the time-domain and/or frequency-domain features of the noise and/or artifacts associated with the sensor movement in the PPG signal can appear similar to those of the PPG itself. Further, the PPG signal processing techniques used for identifying motion artifacts in PPG signals are often complicated and require certain operational controls, such as "Learning Period" and "Re-Learn" action.

The present application provides a new and improved system and method which overcome the above-referenced problems and others.

SUMMARY OF THE INVENTION

In accordance with one aspect, a system for identifying motion artifacts is provided. The system includes a probe measuring a physiological parameter of an associated patient. The probe is positioned on or proximate to the associated patient. An accelerometer positioned on, proximate to, or integrated with the probe measures acceleration. A labeling unit labels measurements of the physiological parameter and temporally corresponding motion characteristics based on the measured acceleration.

In accordance with another aspect, a method for identifying motion artifacts is provided. The method is performed by at least one processor. Measurements of a physiological parameter of an associated patient are received from a probe positioned on or proximate to the associated patient. Further, measurements of acceleration are received from an accelerometer positioned on, proximate to, or integrated with the probe. Measurements of the physiological parameter and temporally corresponding motion characteristics are labeled based on the measured acceleration.

In accordance with another aspect, a system for identifying motion artifacts is provided. The system includes at least one processor programmed to receive measurements of a physiological parameter of an associated patient from a probe positioned on or proximate to the associated patient. Further, measurements of acceleration are received from an accelerometer positioned on, proximate to, or integrated with the probe, and measurements of the physiological parameter are labeled as being with or without motion based on the measured acceleration.

One advantage resides in reducing the number of false alarms.

Another advantage resides in more accurately measuring oxygen saturation and pulse rate or any of the other physiological calculations derived by using photoplethysmographic measurements.

Another advantage resides in a direct way to detect motion artifacts.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

A pulse oximetry system for identifying motion artifacts is provided. The system includes an accelerometer integrated with, positioned on, or positioned proximate to a photoplethysmogram (PPG) sensor, so that movement of the PPG sensor is directly detected. Movement strength and duration can be reliably identified by processing one or more accelerometer signals from the accelerometer. Based on identified movement, physiological measurements, such as oxygen saturation (SpO2) and pulse rate (PR) measurements, produced from the PPG sensor can be sorted as reliable (i.e., motion artifact free) or not-reliable (i.e., subject to motion artifacts). Advantageously, only reliable measurements can be presented to clinicians and/or used for alarming. The identified movement can also be used to indicate how much or little weight should be given to the measured data.

Figure 1:
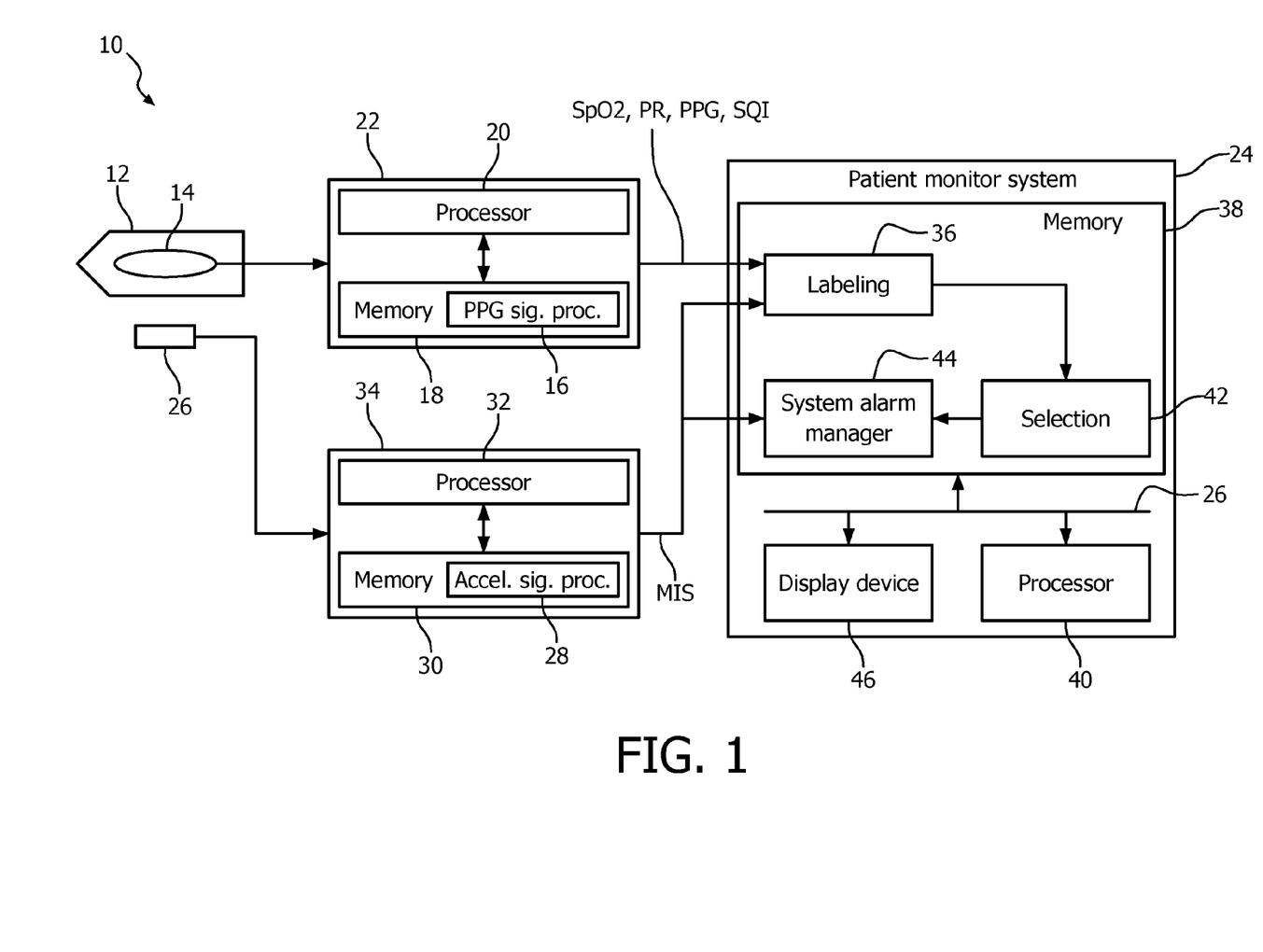
FIG. 1 illustrates an embodiment of a pulse oximetry system.
Figure 2:
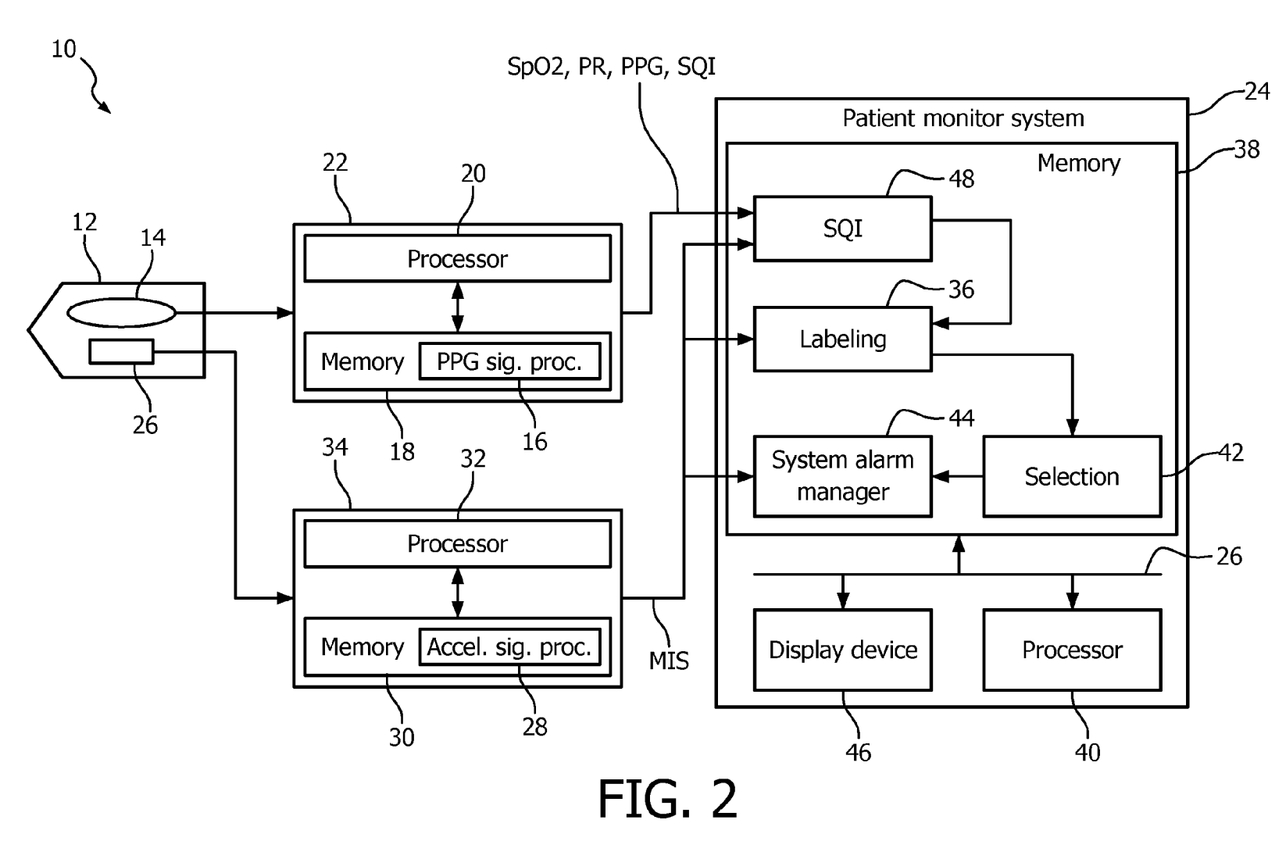
FIG. 2 illustrates another embodiment of a pulse oximetry system.

With reference to FIGS. 1 and 2, a pulse oximetry system 10 includes a PPG probe 12 placed on or around a thin part of an associated patient's body. In the case of an infant, the PPG probe 12 is usually placed across a foot. Otherwise, the PPG probe 12 is usually placed across a fingertip, an earlobe, or on the forehead. The PPG probe 12 includes a sensor 14 with one or more light sources which pass light at red (e.g., around 660 nm) and infrared (e.g., around 940 nm) wavelengths sequentially through the associated patient to a photo-detector. The changing absorbance at each of the two wavelengths is measured to create PPG signals for each of red light and infrared light.

A PPG signal processing unit (PSPU) 16 processes the PPG signals to determine at least one of SpO2, PR, signal quality index (SQI) and PPG. The PSPU 16 processes the PPG signals according to well-known pulse oximetry techniques. For example, SpO2 can be determined based upon the ratio of changing absorbance of the red and infrared light caused by the difference in color between oxygen-bound (bright red) and oxygen-unbound (dark red or blue in severe cases) blood hemoglobin. The PSPU 16 can be software (i.e., processor executable instructions), hardware, or a combination of the two. When the PSPU 16 is, or includes, software, the software is stored on one or more program memories 18 and executed by one or more processors 20, as illustrated.

A pulse oximeter device (POD) 22 positioned proximate to the associated patient, typically at the associated patient's bed, receives the PPG signals from the PPG probe 12. The POD 22 typically includes the PSPU 16, as illustrated. Using the PSPU 16, the POD 22 processes the PPG signals to determine at least one of SpO2, PR, SQI and PPG. However, it is also contemplated that PSPU 16 is remote from the POD 22 within, for example, a patient monitoring system (PMS) 24. In such a case, the POD 22 relays the PPG signals to the PSPU 16. The POD 22 can also be integrated with the PPG probe 12.

An accelometer 26 integrated with, positioned on, or positioned proximate to the PPG probe 12 measures motion to generate one or more accelerator signals. As illustrated in FIG. 1, the accelerometer 26 is positioned proximate to the PPG probe 12, and as illustrated in FIG. 2, the accelerometer 26 is integrated with the PPG probe 12. Typically, the accelerometer 26 is a three-dimensional (3D) or 3-axis accelerometer. However, the accelerometer 26 can measure acceleration in three or less dimensions. The accelerometer signals typically include an accelerator signal for each axis (or dimension) of the accelerometer 26.

An acceleration signal processing unit (ASPU) 28 analyzes the acceleration signals to detect movement of the accelerometer 26. For example, where the acceleration signals include an acceleration signal for each axis of the accelerator 26, a signal-integration process can be used to collect the movement information from each axis. A composite signal can then be formed and thresholded to detect movement of the accelerometer 26. For example, the composite signal can indicate translation along and rotation around each axis. Based on the analysis, the ASPU 28 generates a motion indication signal (MIS).

The MIS can be employed to carry digital messages indicating movement speed, acceleration, direction, duration, and the like. For example, each message can identify motion during a period of movement, and a start and end time for the period of movement. Alternatively, the amplitude of the MIS can be varied to indicate movement strength (i.e., acceleration). Movement strength is typically determined by applying one or more thresholds to the acceleration of the detected movement, where the thresholds identify different movement strengths. For example, a single threshold can be employed to distinguish between no-motion (or insufficient motion) and with-motion (or sufficient motion). As another example, a plurality of thresholds can be employed to distinguish between no-motion, low motion, mediate motion, high motion, and very high motion in any or each direction.

The analysis and generation are suitably performed in parallel with, and independent of, the processing of the PPG signals by the PSPU 16. Further, the ASPU 28 can be software (i.e., processor executable instructions), hardware, or a combination of the two. When the ASPU 28 is, or includes, software, the software is stored on one or more program memories 30 and executed by one or more processors 32, as illustrated.

An accelerometer analysis device 34 positioned proximate to the associated patient, typically at the associated patient's bed, receives the accelerator signals from the accelerometer 26. The accelerometer analysis device 34 typically includes the ASPU 28, as illustrated. Using the ASPU 28, the accelerometer analysis device 34 analyzes the acceleration signals to detect movement of the accelerometer and generates a MIS based on the analysis. However, it is also contemplated that ASPU 28 is remote from the accelerometer device 34 within, for example, the PMS 24. In such a case, the accelerometer analysis device 34 relays the accelerator signals to the ASPU 28. The accelerometer analysis device 34 can also be integrated with the POD 22 and/or the accelerometer 26.

Referring specifically to FIG. 1, one embodiment of the pulse oximetry system 10 includes a labeling unit 36, which receives at least one of SpO2, PR, SQI and PPG from the PSPU 16. The labeling unit 36 further receives the MIS signal from the ASPU 28. As illustrated, the labeling unit 36 is remote from the ASPU 28 and the PSPU 16, and receives the MIS signal and the at least one of SpO2, PR, SQI and PPG separately over wired and/or wireless communication connections.

Based on the MIS signal, the labeling unit 36 labels each of the at least one of SpO2, PR, SQI and PPG with the temporally corresponding motion characteristic, such as with-motion or motion-free, on a beat-by-beat or second-by-second basis. For example, the SpO2 or PR in the current cardiac cycle is labeled as with-motion. Where there is motion, the measurement can further be labeled as associated with low, mediate, high, very high motion, or other motion characteristics. The labeling unit 36 can be software (i.e., processor executable instructions), hardware, or a combination of the two. When the labeling unit 36 is, or includes, software, the software is stored on one or more program memories 38 and executed by one or more processors 40, as illustrated.

A selection unit 42 receives the labeled at least one of SpO2, PR, SQI and PPG, and selects the SpO2 and/or PR measurements which are labeled as motion-free or with acceptable motion characteristics. The SpO2 and/or PR measurements failing to meet these criteria are discarded or marked to be given little weight. Based on the selected SpO2 and/or PR measurements, short-term median SpO2 and/or PR measurements and/or short-term averaged SpO2 and/or PR measurements can be generated. For example, the current SpO2 or PR measurement (for output to user) is the average of a predetermined number of the immediately preceding measurements which are labeled as motion-free. The selection unit 42 can be software (i.e., processor executable instructions), hardware, or a combination of the two. When the selection unit 42 is, or includes, software, the software is stored on the program memories 38 and executed by the processors 40, as illustrated.

A system alarm manager unit (SAMU) 44 generates alarms when one or more of the selected, the average, and the median SpO2 and/or PR measurements meet predetermined alarm criteria. For example, when a selected, average, median, rate of change, or the like SpO2 or PR measurements exceeds a threshold, a threshold for a selected length of time, or other alarm criteria, an alarm is generated. The SAMU 44 can also monitor the associated patient based on the MIS signal. When the MIS signal indicates motion within an immediately preceding period of a predetermined amount of time, such as 10 seconds, the generation of alarms can be suspended. In other words, alarms can only be generated when there is no or an acceptable level of motion for the predetermined amount of time. The SAMU 44 can be software (i.e., processor executable instructions), hardware, or a combination of the two. When the SAMU 44 is, or includes, software, the software is stored on the program memories 38 and executed by the processors 40, as illustrated.

The PMS 24 monitors the associated patient based on one or more of the selected, the average, the median, or the rate of change of SpO2 and/or PR measurements. Using a display device 46, the PMS 24 can present a visual representation of the MIS signal to a user. For example, the current movement strength can be displayed. Further, the PMS 24 can present a visual representation of one or more of the selected, the median, and the average SpO2 and/or PR measurements. For example, the current SpO2 and/or PR measurements can be displayed. As another example, the SpO2 and/or PR measurements can be displayed as trends along with MIS condition. Even more, the PMS 24 can present a visual representation of the generated alarms. The PMS 24 includes the SAMU 44 and can include the labeling and selection units 36, 42, as illustrated. However, it is also contemplated that the POD 22 includes the labeling and selection units 36, 42.

Referring specifically to FIG. 2, another embodiment of the pulse oximetry system 10 is provided. This embodiment is the same as described in the embodiment of FIG. 1, except that it additionally includes an SQI unit 48. The SQI unit 48 receives at least one of SpO2, PR, SQI and PPG from the PSPU 16. The SQI unit 48 further receives the MIS signal from the ASPU 28. As illustrated, the SQI unit 48 is remote from the ASPU 28 and the PSPU 16, and receives the MIS signal and the at least one of SpO2, PR, SQI and PPG separately over wired and/or wireless communications connections. Based on the MIS signal and the at least one of SpO2, PR, SQI and PPG, the SQI unit 48 filters measurements based on SQI before passing the measurements on to the labeling unit 36.

Figure 3:
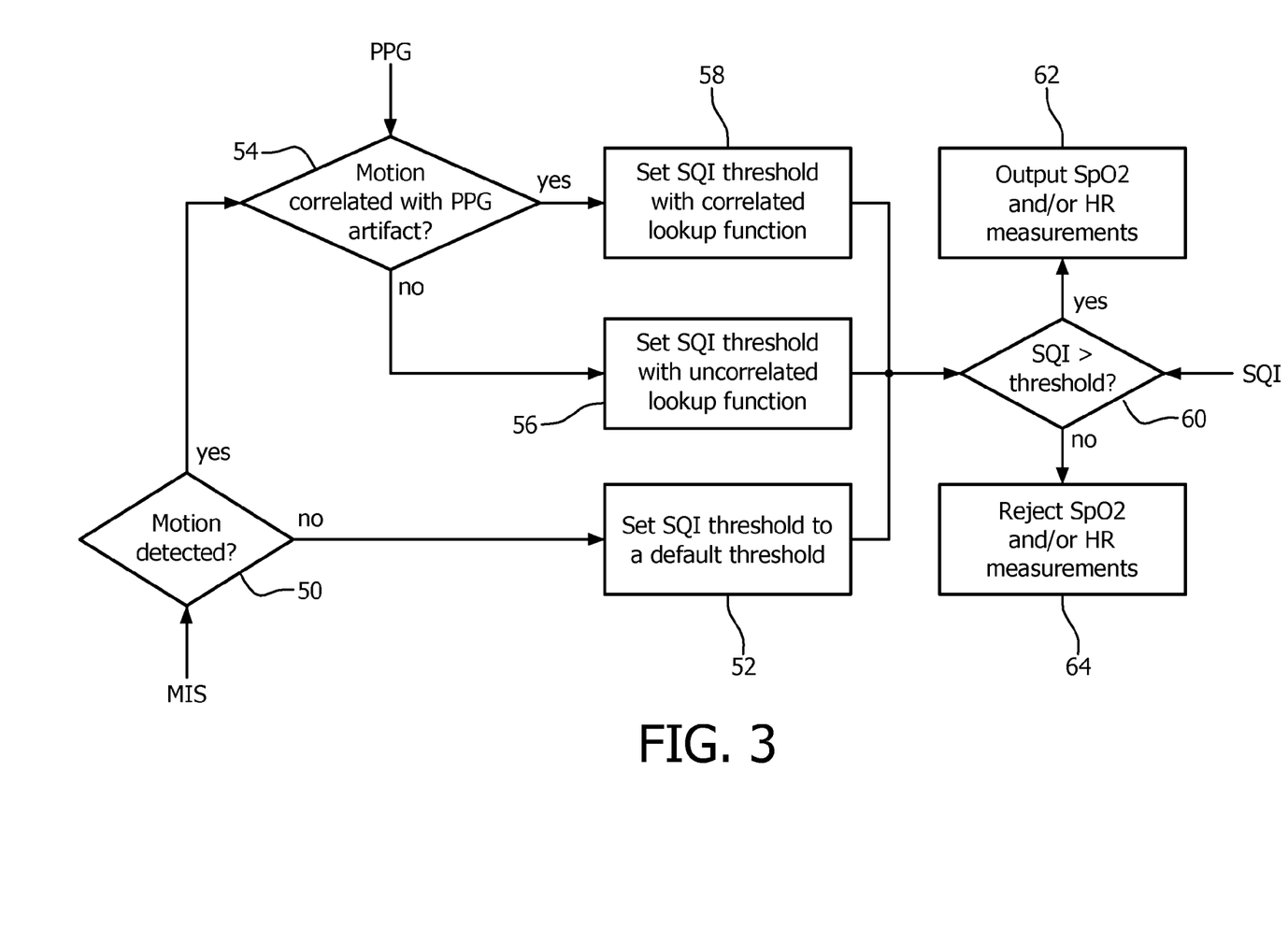
FIG. 3 illustrates a flow chart for thresholding a signal quality index (SQI).

The filtering is suitably made in accordance with the flow diagram of FIG. 3. A determination 50 is made as to whether motion is detected using the MIS signal. Motion is detected when the MIS signal is available and the MIS signal indicates there is motion (or sufficient motion). If there is no motion, the SQI threshold is set 52 to a default, predetermined threshold or other criteria determined by, for example, an operator of the pulse oximetry system 10. If there is motion, a determination 54 is made as to whether the detected motion is correlated to the temporal alignment or frequency content of the PPG.

Figure 4:
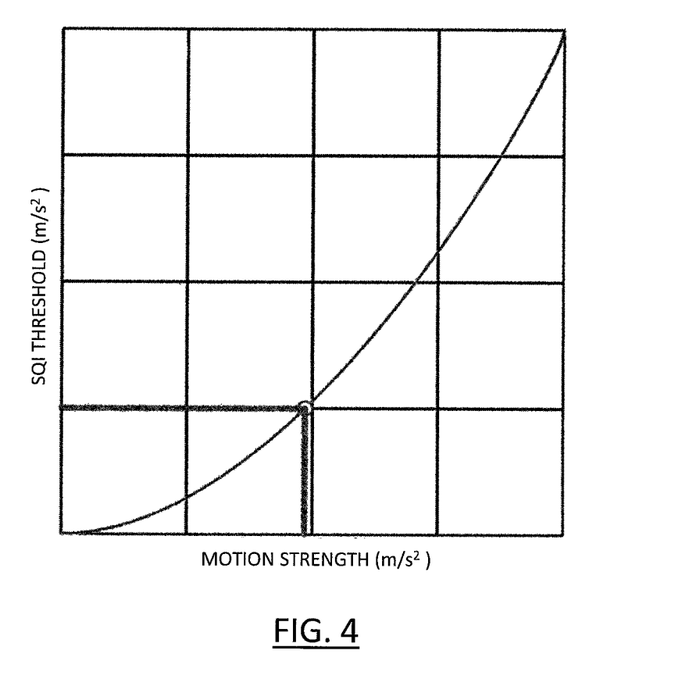
FIG. 4 illustrates an uncorrected motion SQI lookup function.
Figure 5:
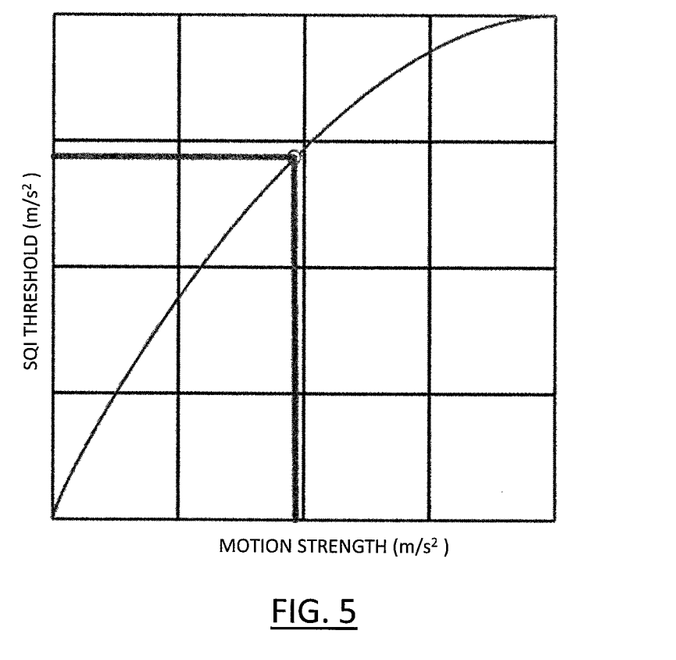
FIG. 5 illustrates a correlated motion SQI lookup function.

If the motion is uncorrelated, an uncorrected motion SQI lookup function is employed to set 56 the SQI threshold. The lookup function is specific to the pulse oximetry system and a function of motion strength. FIG. 4 illustrates a graph of an example of such a lookup function, where the horizontal-axis corresponds to motion strength and the vertical-axis corresponds to SQI threshold. If the motion is correlated, a correlated motion SQI lookup function is employed to set 58 the SQI threshold. The lookup function is specific to the pulse oximetry system and a function of motion strength. FIG. 5 illustrates a graph of an example of such a lookup function, where the horizontal-axis corresponds to motion strength and the vertical-axis corresponds to SQI threshold.

After setting 52, 56, 58 the threshold or other criteria, the threshold or other criteria is compared to the SQI to determine 60 whether the SQI exceeds the threshold or other criteria. If the SQI exceeds the threshold, corresponding measurements, such as PR and SpO2 measurements, are output 62 and employed as described in the first embodiment. In other words, the labeling unit 36 labels the measurements, the selection unit 42 selects measurements without motion or with acceptable motion, or weights measurements with less motion more highly than measurements with more motion, and the SAMU 44 generates alarms based the selected measurements. If the SQI does not exceed the threshold or other criteria, corresponding measurements are discarded 64.

Although the foregoing approach to detecting motion artifacts was described in conjunction with pulse oximetry and pulse rate, it is understood that this approach applies equally well to any of the myriad of other physiological calculations derived by using photoplethysmographic measurements, such as percent saturated carboxyhemoglobin (SpCO), pulse pressure variation (PPV), pulse transient time (PPT), hemoglobin (HB), hemocrit (HCT), glucose (GLU), cholesterol (CHOL), and the like. It is to be appreciated that this approach can also be extended to other types of physiological monitoring, such as electrocardiogram (ECG) monitoring, respiration (RESP) monitoring, and arterial blood pressure (ABP) monitoring. In such embodiments, an accelerometer is placed on each front-end electrode or transducer to sense motion of the electrode or transducer, so any movement (in terms of time, duration, and strength) of the electrode or transducer can be directly and reliably detected. The motion activity detected by the accelerometer can then be used to label the corresponding signal waveform. Further, the parameter measurements derived from the waveform which are associated with the motion will be excluded from output to the end user and from triggering the related alarms. In this way, the accuracy and reliability of the parameter measurements and related alarms will be substantially enhanced.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system for identifying motion artifacts, said system comprising:
    a probe configured to sense a physiological parameter of an associated patient, the probe configured to be positioned on or proximate to the associated patient, the probe being configured to generate one or more physiological signals indicative of the sensed physiological parameter;
    an accelerometer configured to be positioned on, proximate to, or integrated with the probe, the accelerometer configured to generate one or more acceleration signals measuring acceleration;
    a first signal processing unit configured to process the one or more physiological signals from the probe to determine measurements of the physiological parameter;
    a second signal processing unit configured to process one or more acceleration signals from the accelerometer to determine motion characteristics, the processing of the second signal processing unit being performed in parallel, and independent of, the processing of the first signal processing unit; and
    a labeling unit configured to label measurement of the physiological parameter with temporally corresponding motion characteristics based on the determined motion characteristics; and
    a signal quality index (SQI) threshold unit configured to discard or down weight measurements of the physiological parameter with signal quality indices (SQI)s below a SQI threshold and passing a remaining or down weighted measurements of the physiological parameter to the labeling unit; and wherein the SQI threshold unit is configured to determine the SQI threshold by:
        determining whether there is motion based on the measured acceleration;
        in response to determining there is no motion, setting the SQI threshold to a predetermined value;
        in response to determining there is motion, determining whether the motion is correlated with a measured motion artifact of the one or more physiological signals that is generated by, and received from, the probe;
        in response to determining the motion is correlated, setting the SQI threshold to a first value using a correlated lookup function of a motion strength value; and
        in response to determining the motion is uncorrelated, setting the SQI threshold to a second value using an uncorrelated lookup function of the motion strength value.

2. The system according to claim 1, wherein the second signal processing unit is further configured to generate a motion information signal (MIS) from the determined motion characteristics, an amplitude of the MIS corresponding to the measured acceleration.

3. The system according to claim 2, wherein the second signal processing unit is further configured to generate the MIS to include at least one of:
    digital messages indicating at least one of movement speed, acceleration, direction, and duration; and
    digital messages that each identify a start and end time for a period of movement.

4. The system according to claim 1, further including:
    an alarm unit configured to generate alarms based on the measurements of the physiological parameter labeled with temporally corresponding motion characteristics that are indicative of acceptable motion characteristics.

5. The system according to claim 4, wherein the alarm unit is configured to disable the generation of alarms for a predetermined period of time in response to motion characteristics indicative of a motion indication signal (MIS) exceeding a predetermined threshold.

6. The system according to claim 5, wherein the accelerometer is configured to measure acceleration in three-dimensions and the MIS signal is indicative of translation along and rotation around each axis.

7. The system according to claim 1, further including:
a display device configured to display measurements of the physiological parameter and a visual representation of a motion indication signal (MIS).

8. The system according to claim 7, wherein the physiological parameter is one of oxygen saturation (SpO2), pulse rate (PR), percent saturated carboxyhemoglobin (SpCO), pulse pressure variation (PPV), pulse transient time (PPT), hemoglobin (HB), hemocrit (HCT), glucose (GLU), and cholesterol (CHOL).

9. The system according to claim 1, further including:
a selection unit configured to discard measurements of the physiological parameter labeled with unacceptable motion characteristics.

10. A method for identifying motion artifacts, said method comprising:
receiving, by at least one processor, one or more physiological signals of a sensed physiological parameter of an associated patient from a probe configured to be positioned on or proximate to the associated patient;
receiving, by the at least one processor, one or more acceleration signals measuring acceleration from an accelerometer positioned on, proximate to, or integrated with the probe;
processing the one or more physiological signals received from the probe to determine measurements of the physiological parameter;
processing the one or more signals from the accelerometer to determine motion characteristics, the processing of the one or more physiological signals being performed in parallel, and independent of, the processing of the one or more acceleration signals;
labeling, by the at least one processor, measurements of the physiological parameter with temporally corresponding motion characteristics based on the determined motion characteristics; and
generating, with the at least one processor, a signal quality index (SQI) of the measured physiological parameter by operations including
determining whether there is motion based on the measured acceleration;
in response to determining there is no motion, setting (SQI) threshold to a predetermined value;
in response to determining there is motion, determining whether the motion is correlated with a measured motion artifact of the one or more physiological signals that is generated by, and received from, the probe;
in response to determining the motion is correlated, setting the SQI threshold to a first value using a correlated lookup function of a motion strength value; and,
in response to determining the motion is uncorrelated, setting the SQI threshold to a second value using an uncorrelated lookup function of the motion strength value.

11. The method according to claim 10, further including:
displaying measurements of the physiological parameter and a visual representation of a motion indication signal (MIS).

12. The method according to claim 10, wherein the physiological parameter is one of oxygen saturation (SpO2), pulse rate (PR), percent saturated carboxyhemoglobin (SpCO), pulse pressure variation (PPV), pulse transient time (PPT), hemoglobin (HB), hemocrit (HCT), glucose (GLU), and cholesterol (CHOL).

13. The method according to claim 10, further including at least one of:
generating a motion information signal (MIS) from the determined motion characteristics, an amplitude of the MIS corresponding to the measured acceleration; and
generating the MIS to include digital messages indicating at least one of movement speed, acceleration, direction, and duration.

14. The method according to claim 13, further including:
generating alarms based on the measurements of the physiological parameter labeled with temporally corresponding motion characteristics that are indicative of acceptable motion characteristics; and
disabling of alarms for a predetermined period of time in response to the motion characteristics indicative of the MIS exceeding a predetermined threshold.

15. The method according to claim 14, further including:
discarding measurements of the physiological parameter that are labeled as not being indicative of acceptable motion characteristics.

16. A system for identifying motion artifacts, said system comprising:
at least one processor programmed to:
receive measurements of a physiological parameter of an associated patient from an associated probe configured to be positioned on or proximate to the associated patient;
receive measurements of acceleration from an associated accelerometer positioned on, proximate to, or integrated with the probe;
label measurements of the physiological parameter as being with or without motion based on a measured acceleration threshold; and
discard or down weight measurements of the physiological parameter with signal quality indices (SQI)s below a SQI threshold, the at least one processor being programmed to determine the signal quality index threshold by:
determining whether there is motion based on the measured acceleration;
in response to determining there is no motion, setting the SQI threshold to a predetermined value;
in response to determining there is motion, determining whether the motion is correlated with a measured motion artifact of the one or more physiological signals that is generated by, and received from, the probe;
in response to determining the motion is correlated, setting the SQI threshold to a first value using a correlated lookup function of a motion strength value; and
in response to determining the motion is uncorrelated, setting the SQI threshold to a second value using an uncorrelated lookup function of the motion strength value.

17. The system according to claim 16, further including:
a probe configured to sense the physiological parameter of the associated patient, the probe being configured to generate one or more physiological signals indicative of the sensed physiological parameter;
an accelerometer configured to be positioned on, proximate to, or integrated with the probe, the accelerometer configured to generate one or more acceleration signals measuring acceleration; and wherein the at least one processor is further programmed to:
process the one or more physiological signals from the probe to determine measurements of the physiological parameter;
process one or more acceleration signals from the accelerometer to determine motion characteristics, the processing of the acceleration signals being performed in parallel, and independent of, the processing of the physiological signals; and
label measurements of the physiological parameter with temporally corresponding motion characteristics based on the determined motion characteristics.

* * * * *